(12) United States Patent
Einarsson

(10) Patent No.: US 7,935,068 B2
(45) Date of Patent: May 3, 2011

(54) ORTHOPEDIC OR PROSTHETIC SUPPORT DEVICE

(75) Inventor: Palmi Einarsson, San Juan Capistrano, CA (US)

(73) Assignee: Ossur HF, Reykjavik (IS)

(*) Notice: Subject to any disclaimer, the term of this patent is extended or adjusted under 35 U.S.C. 154(b) by 221 days.

(21) Appl. No.: 12/195,798

(22) Filed: Aug. 21, 2008

(65) Prior Publication Data

US 2009/0054819 A1  Feb. 26, 2009

Related U.S. Application Data

(60) Provisional application No. 60/935,628, filed on Aug. 23, 2007.

(51) Int. Cl.
*A61F 5/00* (2006.01)

(52) U.S. Cl. .............. 602/26; 602/23; 602/5; 602/1; 602/27; 602/29

(58) Field of Classification Search ............ 602/26, 602/23, 5, 1, 27–29
See application file for complete search history.

(56) References Cited

U.S. PATENT DOCUMENTS

| | | | |
|---|---|---|---|
| 187,428 A | 2/1877 | Sutton | |
| 958,267 A | 5/1910 | Martin | |
| 2,203,235 A | 6/1940 | Portnow | |
| 5,178,137 A | 1/1993 | Goor et al. | |
| 5,370,133 A | 12/1994 | Darby et al. | |
| 6,221,035 B1 | 4/2001 | Kana et al. | |
| 6,317,888 B1 | 11/2001 | McFarlane | |
| 6,398,747 B1 | 6/2002 | Rudy, Jr. et al. | |
| 7,198,610 B2 | 4/2007 | Ingimundarson et al. | |
| 2002/0107464 A1 | 8/2002 | Castillo | |
| 2003/0187375 A1* | 10/2003 | Gaylord | 602/26 |
| 2005/0240130 A1 | 10/2005 | Rudy | |
| 2005/0283102 A1* | 12/2005 | Schwenn et al. | 602/5 |
| 2006/0052731 A1 | 3/2006 | Shimada et al. | |
| 2006/0135901 A1 | 6/2006 | Ingimundarson | |
| 2006/0173391 A1 | 8/2006 | Bodenschatz | |
| 2007/0038169 A1 | 2/2007 | Alon et al. | |
| 2007/0050877 A1 | 3/2007 | Rampersad | |
| 2007/0060853 A1 | 3/2007 | Sindel et al. | |
| 2008/0146981 A1* | 6/2008 | Greenwald et al. | 602/13 |
| 2008/0249448 A1* | 10/2008 | Stevenson et al. | 602/16 |

FOREIGN PATENT DOCUMENTS

GB   2 433 204 A   6/2007

OTHER PUBLICATIONS

M2 Closure Systems and Components Catalog <http://www.m2intl.com/medical/MedicalCat htm>.

* cited by examiner

*Primary Examiner* — Patricia M Bianco
*Assistant Examiner* — Tarla R Patel
(74) *Attorney, Agent, or Firm* — Bacon & Thomas, PLLC

(57) ABSTRACT

An orthopedic or prosthetic support device is arranged to conform and secure to a limb of a wearer. The device includes a resilient support member adapted to extend about a limb, and a tensioning element associated with the support member. An adjustment system is connected to the support member and engages the tensioning element. The adjustment system is arranged to incrementally adjust and retain the tensioning element relative to the support member.

11 Claims, 4 Drawing Sheets

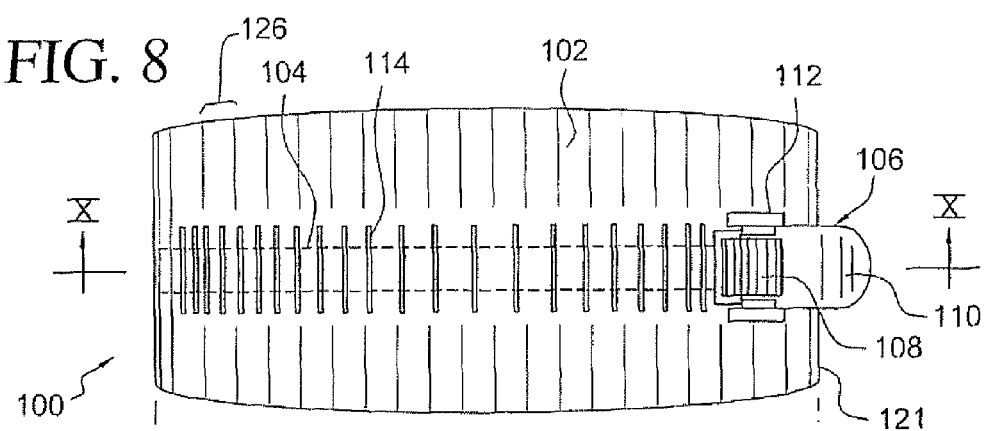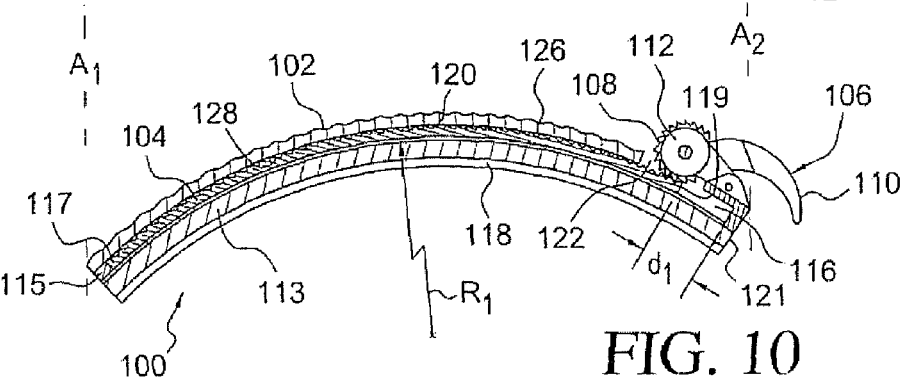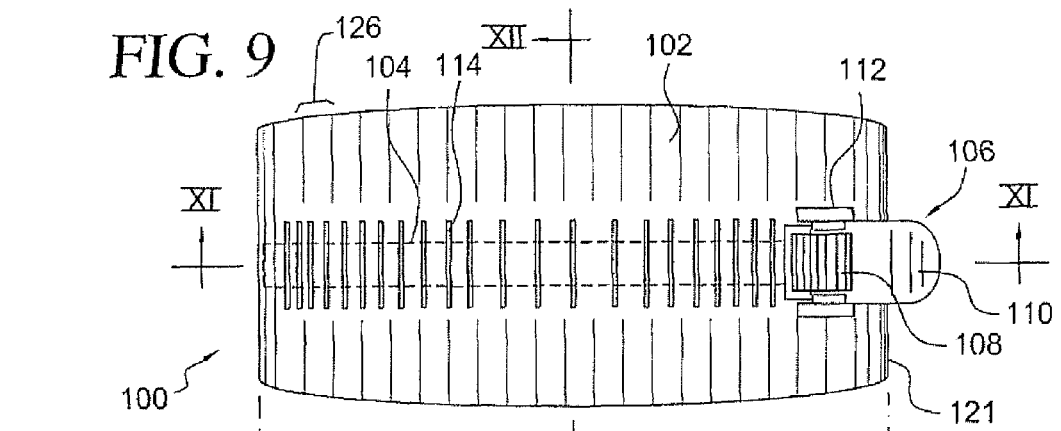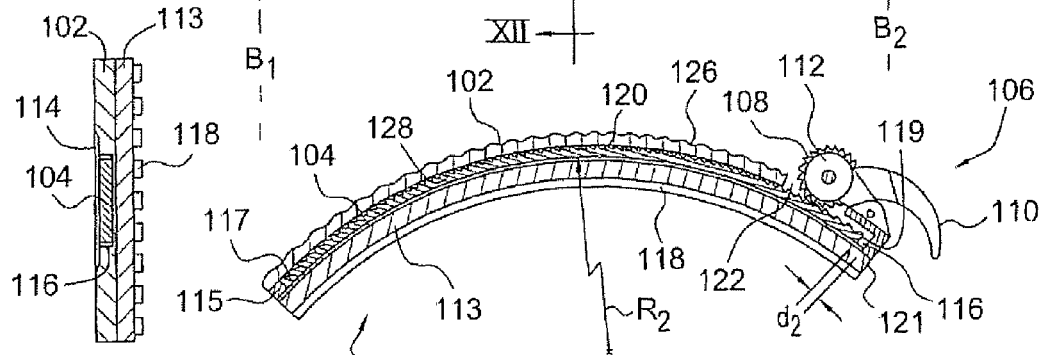

ORTHOPEDIC OR PROSTHETIC SUPPORT DEVICE

CROSS-REFERENCE TO RELATED APPLICATION

This application claims the benefit of priority from U.S. Provisional Application No. 60/935,628, filed on Aug. 23, 2007.

FIELD OF THE INVENTION

This invention relates to support devices for use in orthopedic and prosthetic systems. Particularly, the orthopedic and prosthetic support devices described herein are arranged for providing support at incremental levels on the anatomy of the wearer in replacement of or in supplement to strapping systems.

BACKGROUND

In many orthopedic and prosthetic systems, straps are employed for securing elements to the anatomy of the wearer. Such straps may prove cumbersome to the wearer to apply, and may also be difficult for some wearers to adjust.

While there have been attempts to overcome such shortcomings, many solutions are complicated and add bulk to components such that additional structure is provided which may protrude from any orthopedic or prosthetic device. Further, many of such solutions, merely provide an alternative to a strap and do not both replace a strap and provide bracing support.

Thus, there is a need that exists for an orthopedic or prosthetic support device that makes donning and doffing easy in a streamlined manner, yet enables sufficient support to the limb of the wearer.

SUMMARY

In accordance with an exemplary embodiment of the invention, an orthopedic device comprises a substantially rigid frame member, a resilient support member mounted to the frame member, and an elongate tensioning element associated with the support member. The tensioning element defines first and second ends such that the first end is fixedly secured to the support member and the second end is movable relative to the support member. The tensioning element is preferably arranged in a longitudinal direction of the support member.

The brace further includes an adjustment system that is connected to the support member and engages the tensioning element second end. The adjustment system is arranged to incrementally adjust and retain the tensioning element second end relative to the support member. The frame member may be mountable on a human limb solely by the support member. The support member is adapted to securely fit and conform to the human limb via adjustment of the tensioning element by the adjustment system.

The support member can simultaneously provide support by distributing forces exerted on a limb, and serve to secure itself and other components to the limb of the wearer.

According to one variation of the embodiment, the tensioning element is located and retained within a channel defined by the support member. The tensioning element defines an anchor located at the first end and is fixedly secured to the support member. This embodiment is particularly advantageous in that the tensioning element does not protrude from the support member, and does not add additional bulk to the support member, thereby contributing to and/or maintaining a streamlined support member which is not materially altered from a support member without the tensioning element.

The adjustment system may include a ratcheting device that includes a rotational device and a handle. Adjustment of the handle permits incremental adjustment of the tensioning element relative to the support member. The handle may be mounted on a frame member and the ratcheting device is supported within or by the fame member, and arranged to engage the tensioning member.

The support member may define a plurality of openings and material portions surrounding the openings. The tensioning element may be arranged to extend through only the material portions of the support member in a channel defined therein. The support member may define a main body having a main thickness. The main body may have a plurality of localized sections defined by a reduced thickness relative to the main thickness thereby accommodating bending of the support member as the tensioning element is adjusted in order to better conform to the limb of the wearer. The reduced thickness sections are generally arranged perpendicular to the direction of the tensioning element. The reduced thickness sections are particularly advantageous in part to enhance the resiliency in a bending direction toward the anatomy of the wearer, without increasing bending capabilities away from the anatomy.

According to another exemplary embodiment, the frame member defines first and second segments depending from a central portion, and the support member defines first and second segments. The support member is secured to the frame member central portion and the first and second segments extend therefrom. The adjustment system is secured to the central portion and is connected to the tensioning element. The tensioning element includes first and second cables wherein the first cable corresponds to the first support member segment, and the second cable corresponds to the second support member segment.

In yet another embodiment, a first surface of the support member is secured to the frame member and a second surface of the support member opposite the first surface includes a frictional feature. The frictional feature may be padding or compressible material having a perforated silicone or frictional foam type material. Alternatively, a silicone or foam type coating may be applied directly to the support member without any additional padding material, and of a thickness sufficient to provide some form of padding alone from the silicone or foam type material. Advantageously, in combination with the bending caused by the tensioning member, the frictional feature assists in maintaining the support member on the wearer without additional strapping means.

According to another embodiment, an orthopedic or prosthetic device comprises a flexible support member having a curved segment, and a first end. The device also includes an elongate tensioning element associated with the curved segment of the support member. The tensioning element may have first and second ends, wherein the first end is anchored to the support member first end. The device also has an adjustment system which is connected to the support member and the tensioning element second end. The adjustment system is adapted to rotatably adjust the position of the tensioning element second end relative to the support member thereby adjusting the curvature of the curved segment.

A frictional feature, either applied directly to the support member or via padding to the support member, is provided in combination with these features to prevent any slippage of the support member when it is secured onto anatomy.

BRIEF DESCRIPTION OF THE DRAWINGS

These and other features, aspects, and advantages of the present invention will become better understood with regard to the following description, appended claims, and accompanying drawings.

FIG. 8 is a perspective view of another embodiment of an orthopedic device in an "open" configuration.

FIG. 9 is a perspective view of the orthopedic device according to FIG. 8 in a "closed" configuration.

FIG. 10 is a sectional view taken along line X-X in FIG. 8.

FIG. 11 is a sectional view taken along line XI-XI in FIG. 9.

FIG. 12 is a sectional view taken along line XII-XII in FIG. 9.

DESCRIPTION OF VARIOUS EMBODIMENTS

A. Overview

Figure 1:
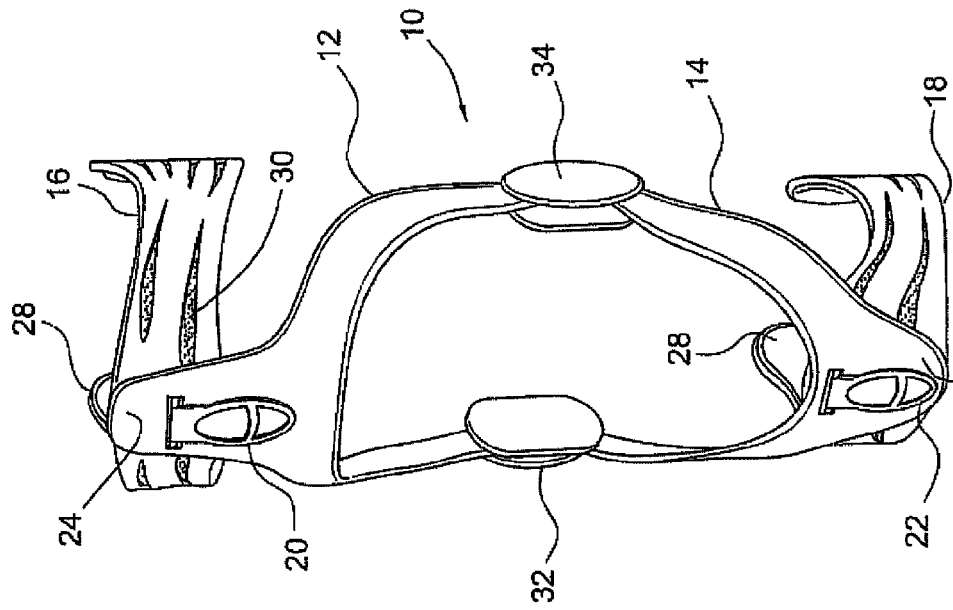
FIG. 1 is a perspective view of an embodiment of an orthopedic brace showing support members in an "open" configuration.
Figure 2:
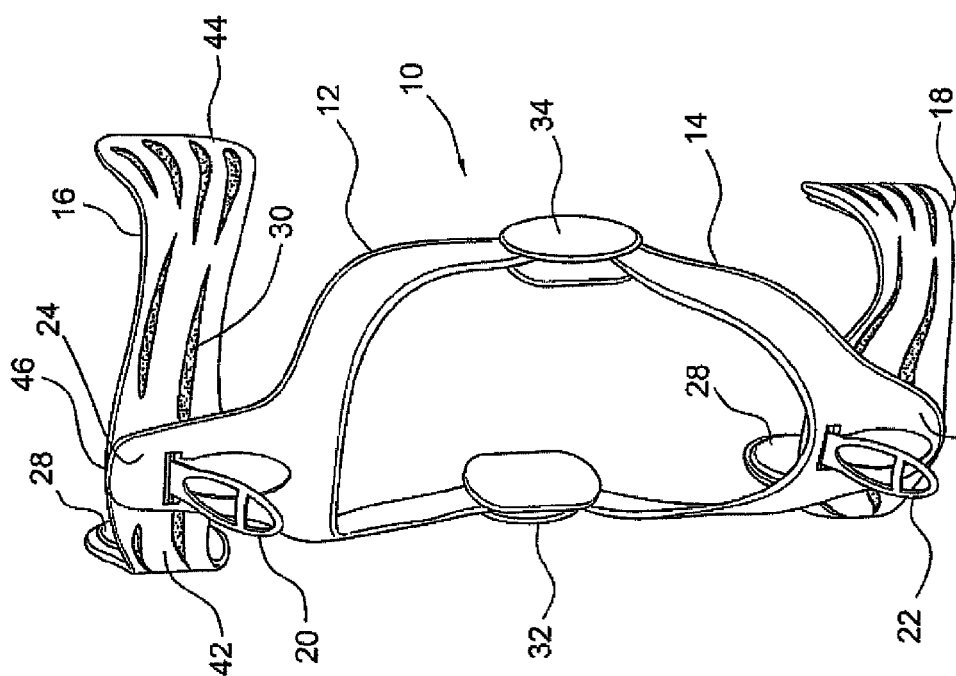
FIG. 2 is a perspective view of the orthopedic brace according to FIG. 1 showing the support members in a "closed" configuration.
Figure 4:
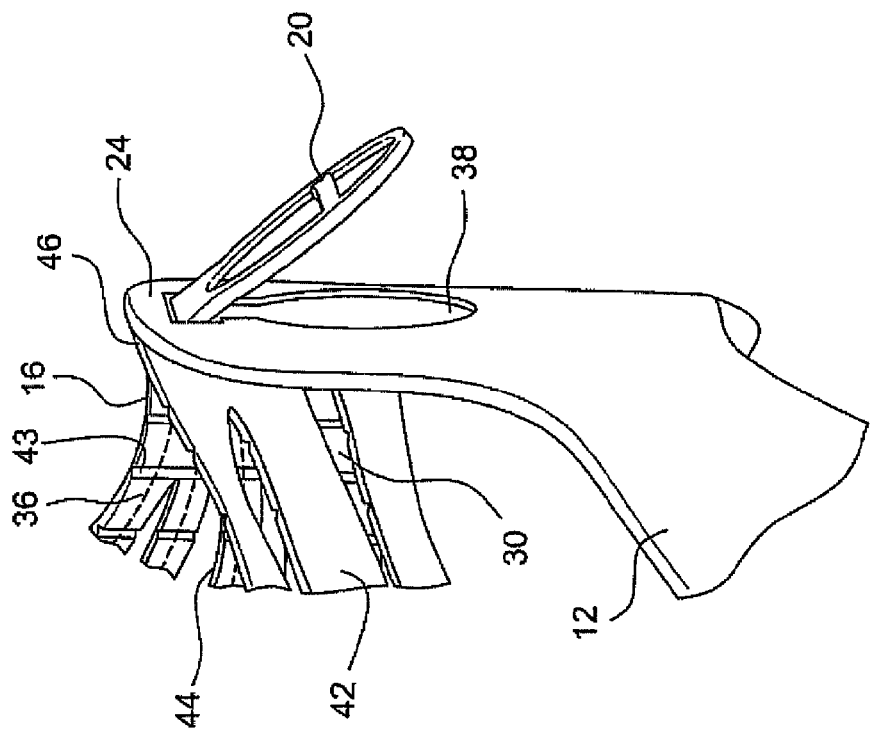
FIG. 4 is a sectional view of the orthopedic brace according to FIG. 1 showing support members in a "closed" configuration.
Figure 3:
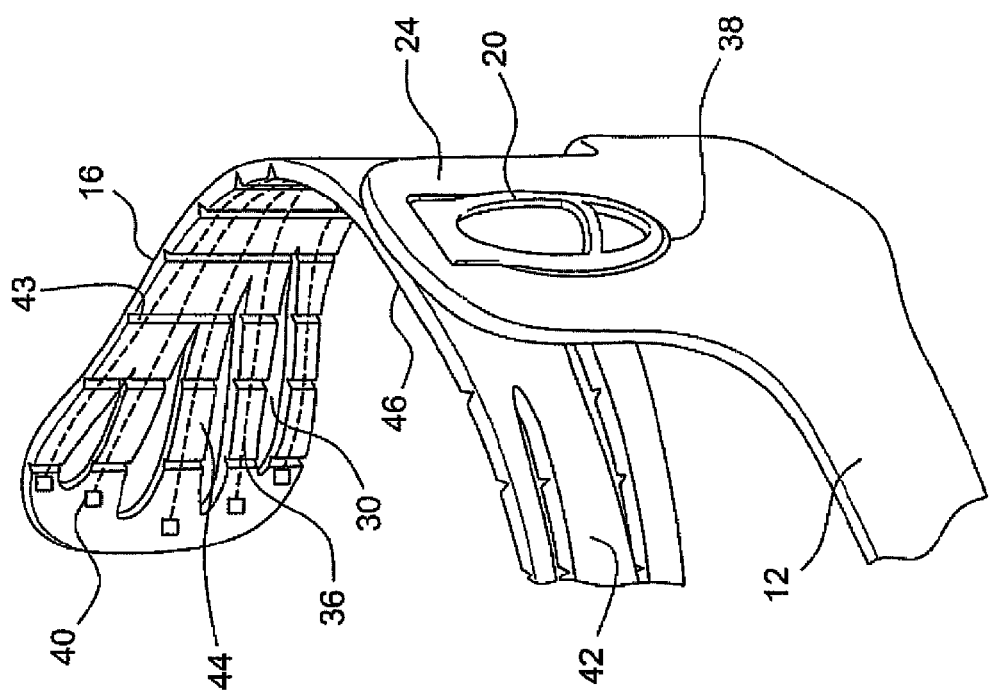
FIG. 3 is a sectional view of the orthopedic brace according to FIG. 1 showing support members in an "open" configuration.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

B. Environment and Context of Embodiments

Numerous orthopedic and prosthetic support member embodiments are described herein, with an exemplary discussion given to braces directed to the knee joint and surrounding areas. The orthopedic and prosthetic support member embodiments may serve in preventative or remedial capacities. While the orthopedic and prosthetic devices is described within the context of a preferred embodiment that is directed to securing the knee joint, many of the features described herein may be extended to orthopedic braces that secure other joints and body parts, such as the wrist, elbow, shoulder, ankle and neck.

The brace embodiments and features thereof may be dimensioned to accommodate different types, shapes and sizes of human joints and appendages. In addition, embodiments may be modified to orient principal forces exerted by strap systems of the embodiments at any desirable location to secure the brace onto a leg in order to stabilize the knee.

For explanatory purposes, each orthopedic or prosthetic system embodiment or component thereof described herein is divided into sections which are denoted by general anatomical terms for the human body. Such anatomical terms are provided to distinguish various elements of the brace embodiments from one another, but which are not to be considered to limit the scope of the invention.

Each of these terms is used in reference to a human leg, by way of example, which is divided in similar sections with a proximal-distal plane generally extending along the meniscus of the knee between the femur and tibia. The terms "proximal" and "distal" generally refer to locations of the brace that correspond to the location of leg relative to the point of attachment of the leg to the body. The terms "upper" and "lower" may be used in combination with "proximal" and "distal" to connote gradations in location of "proximal" and "distal." The location at where the brace corresponds to the knee joint is used herein to generally delimit the proximal and distal sections of the brace.

The embodiments of the knee brace can also be considered to fall within "anterior" and "posterior" sections by an anterior-posterior plane. The anterior-posterior plane generally corresponds to the coronal or frontal plane of a human leg which lies along the central longitudinal axis of a body. A posterior side or element is therefore located behind this anterior-posterior plane, whereas an anterior side or element is located in front of the anterior-posterior plane.

The term "inwardly" is commonly used herein to distinguish the side of the brace that may direct to the posterior side of the brace and specifically adjacent to the leg of the wearer of the brace. Contrariwise, the term "outwardly" is the used to denote the side of the brace that is opposite to the inwardly side.

The terms "medial" and "lateral" are relative terms that are generally understood as indicating location near the midsaggital plane or midline. Therefore, elements that are located near the midline are referred to as "medial" and those elements that are further from the midline are considered to be "lateral." The term "central" is used to denote the area along the midline of a joint thereby dividing and sharing regions of the medial and lateral regions.

From these terms, it follows that the anterior section of the brace has the following quadrants: (I) proximal-medial, (II) distal-medial, (III) distal-lateral, and (IV) proximal-lateral. The posterior section of the brace has the following quadrants: (V) proximal-medial, (VI) distal-medial, (VII) distal-lateral, and (VIII) proximal-lateral. Structural members and features thereof will fall within one of the quadrants is specifically referenced in relation to such quadrant, either in its entirety or partially.

The terms "rigid" and "flexible" are repeatedly used herein to distinguish characteristics of portions of the brace. The term "rigid" is intended to denote that the frame is devoid in flexibility. Within the context of frame members that are "rigid," it is intended to indicate that they may break if bent with sufficient force. On the other hand, the term "flexible" is intended to denote that features are capable of repeated bending. The term "resilient" is used to qualify such features are generally returning to the initially molded shape without permanent deformation. Yet, such resiliency is considered to provide some resistance to bending and thereby provide some degree of support.

The anatomical and characteristic terms described herein are not intended to detract from the normal understanding of such terms as readily understood by one of ordinary skill in the art of orthotics. Moreover, the elements of the embodiments described herein are intended to embrace embodiments that generally correspond to the aforementioned anatomical sections. In other words, it is understood that the elements of the brace embodiments described herein may deviate from falling exactly within the confines of the aforementioned anatomical sections.

C. Various Embodiments of the Orthopedic and Prosthetic Device

In observing the embodiment of FIGS. 1-4, an embodiment of an orthopedic or prosthetic system for use with the support device is shown and generally designated 10. For explanation purposes, the orthopedic or prosthetic system 10 is a knee brace configured for securing to a leg of a user. While depicted in the context of a knee brace, it is readily apparent to the skilled artisan from the discussion herein that the orthopedic and prosthetic support device and particular features thereof of the present invention may be adapted to be secured other parts of the body to treat joints apart from the knee.

The orthopedic brace 10 comprises substantially rigid proximal and distal frame members 12, 14, that are connected to one another by rotational hinges 32, 34. The proximal and distal frame members 12, 14 preferably have arcuate configurations which are arranged to accommodate the contours of a leg. In addition, the proximal and distal frame members 12, 14 define proximal and distal central portions 24, 26, respectively, generally defined at a central or mid-span portion of the proximal and distal frame members 12, 14.

The orthopedic brace 10 includes substantially flexible and arcuate support members 16, 18 that are mounted to a posterior surface of the frame members 12, 14, respectively. The support members 16, 18, as FIG. 2 contrasted with FIG. 1, are arranged to be adjusted in curvature, thereby permitting conformance to and adjustment for sizes on a leg, and be adjusted to the degree to secure to a leg without circumferential straps. While flexible, these support members 16, 18 may be constructed from resilient material and have openings 30 to provide ventilation of the support members.

The support members 16, 18 of this embodiment have first and second segments 42, 44 which depend from a central portion 46 secured to the central portions 24, 26 of the frame members. The first and second segments 42, 44 extend outwardly from the central portions 24, 26 so as to flex relative to the central portions 24, 26.

The orthopedic device 10 also includes a plurality of tensioning elements 36 that are associated with the support members 16, 18. These tensioning elements 36, such as cables or bands, each have a first end 40 that is anchored to an extreme end of a respective segment 42, 44 of the support members 16, 18. In this embodiment, the tensioning elements 36 are preferably located within the material portions of the support members 16, 18 which are contrasted from the openings 30. The tensioning elements 36 are configured to be moved relative to the support members 16, 18, and thereby cause the support members 16, 18 to adjust in curvature in response to movement of the tensioning elements 36.

The orthopedic brace 10 further defines proximal and distal adjustment systems 20, 22 which are mounted on the center portions 24, 26, and coupled to a second end (opposite the first end) of the tensioning elements 36. As will be defined in reference to other embodiments described below, the adjustment systems 20, 22 are arranged to incrementally adjust the curvature of the support members 16, 18 by regulating the position of the second end of the tensioning elements relative to the support members 16, 18.

The adjustment systems 20, 22 may be arranged so as to be housed within a recess 38 formed on the frame members 12, 14 so as to contribute to a streamlined brace without protruding features. While the adjustment systems 20, 22 may be withdrawn from the recess when incrementally adjusting the tensioning elements, they are stored within the recess 38 when the tensioning elements are maintained at an appropriate setting. This provides a generally continuous structure without gaps, raised areas, sharp edges and other protuberances or recesses that may cause discomfort to the wearer of the brace. Further, it prevents elements protruding from the brace which may catch on objects.

A frictional feature is preferably provided on the support members by way of ventilated padding 28 having a coating of silicone. An exemplary padding material that may be used is described in U.S. patent application Ser. No. 11/723,604, entitled "Spacer Element for Prosthetic and Orthotic Devices," and owned by the assignee of this disclosure. U.S. patent application Ser. No. 11/723,604 is incorporated herein by reference.

The orthopedic device 10 may function without circumferential straps that are common to many orthopedic devices or such conventional straps may be used in supplement to the support members. The support members 16, 18 are incrementally sized by selective adjustment of the adjustment systems 20, 22. The adjustment systems 20, 22, may include a ratcheting device housed within the frame members and which engages or winds the tensioning members 36 associated with the support members 16, 18 so as to reduce or enlarge the curvature of the support members 16, 18 against the leg of the wearer. The adjustment systems 20, 22 may be set so that the tensioning members are securely tightened to the leg to a degree which will maintain the brace on the leg.

The frictional feature, such as padding 28, may be used to additionally maintain the support members 16, 18 on the leg due to the combination of the tight and conforming fit of the support members and the engagement of the frictional feature on the leg. Further, since the support members include openings, and the frictional feature is preferably perforated, the support members may be sized in a manner that is sufficiently larger than conventional securing straps so as to provide more surface area to grip the leg while allowing for sufficient ventilation of the leg.

Turning specifically to the individual features of the brace 10, the proximal and distal frame members 12, 14 preferably have arcuate configurations which are arranged to accommodate the contours of a leg. Preferably, in the embodiment of FIGS. 1-4, the proximal and distal frame members do not yield to the contours of the leg but instead are preformed to a particular shape that accommodates the leg. When worn, the proximal and distal frame assemblies are intended to be shaped so as to closely secure to the leg.

The proximal and distal frame members 12, 14 are each preferably constructed from a unitary or continuous rigid piece of material. The frame 12 may be characterized herein as being substantially rigid. The rigidity of the frame is generally the result of both the material from which the frame is constructed from and its geometry.

The material and geometry of the proximal and distal frame members are generally rigid along the entirety of their length such that rigidity of the frame assemblies has a generally high and uniform rigidity. Exemplary materials that may be used for constructing the frame include metals such as aluminum, titanium, and steel, thermoset resin composite systems including glass or carbon fibers, and thermoplastics that have been rendered rigid by way of material composition and geometry of the frame members.

It will be noted that the requirement that the frame members have substantially rigid properties is provided only as an exemplary configuration. It will be noted that the frame may have flexible properties, and may further be provided in discrete segments such that the proximal and distal frame assemblies are segmented as opposed to continuous, and may be connected to one another by suitable hinges, fasteners or other suitable elements.

For a more complete description of the frame members and rotational hinges that may be used in combination with any of the embodiments provided herein is described in co-pending U.S. application Ser. No. 12/068,783, entitled "ORTHOPEDIC BRACE INCLUDING A PROTECTOR ASSEMBLY" and owned by the assignee of this disclosure. U.S. application Ser. No. 12/068,783 is incorporated herein by reference.

In the embodiment of FIGS. 1-4, the support member 16, 18 is substantially more flexible than the rigid frame 12. For example, while the rigid frame 12 does not yield to the leg when worn, the support members 16, 18 is sufficiently flexible so as to bend so as to conform to the legs.

In order to increase the bending of the support members 16, 18, they may be provided with reduced thickness portions 43 which facilitate bending about the anatomy upon which the support members are secured. Particularly, in the example in FIGS. 3 and 4, the portions 43 are formed along the surface of the support members 16, 18 intended to be adjacent to the anatomy of the wearer so as to enhance the direction of the bending.

A variety of materials may be employed to construct the support members The support members may be constructed from materials such as TRIAX (abs/nylon blend), polypropylene, polyethylene, nylon, carbon or glass fiber prepeg with thermosetting or thermoplastic resins, and rigid foam from EVA, platezote or polyurethane. The support member may also be constructed from a generally resilient and breathable textile and reinforced with a frame. Such a frame may be formed from a substantially resilient material.

The support members may be constructed in any manner of the sub-shells taught in U.S. application Ser. No. 12/068,783, so as to include pressure-relieving perimeter edge portions.

In a variation of this embodiment, the cables may be formed from a shape memory material, such as NITINOL or a shape memory polymer. According to this variation, the shape memory based cable or band has a molded or imparted shape that is necessary to secure the support member to a leg. Upon an application of heat or a current onto the shape memory cables of the support member, the shape of the support member opens allowing for the brace to be removed from the leg of the wearer. In another variation, the molded or imparted shape (to which the cable or band returns to in shape) is the open configuration. It follows that upon application of heat or a current to the cable or band allows for the support member to be shaped onto the leg.

Figure 5:
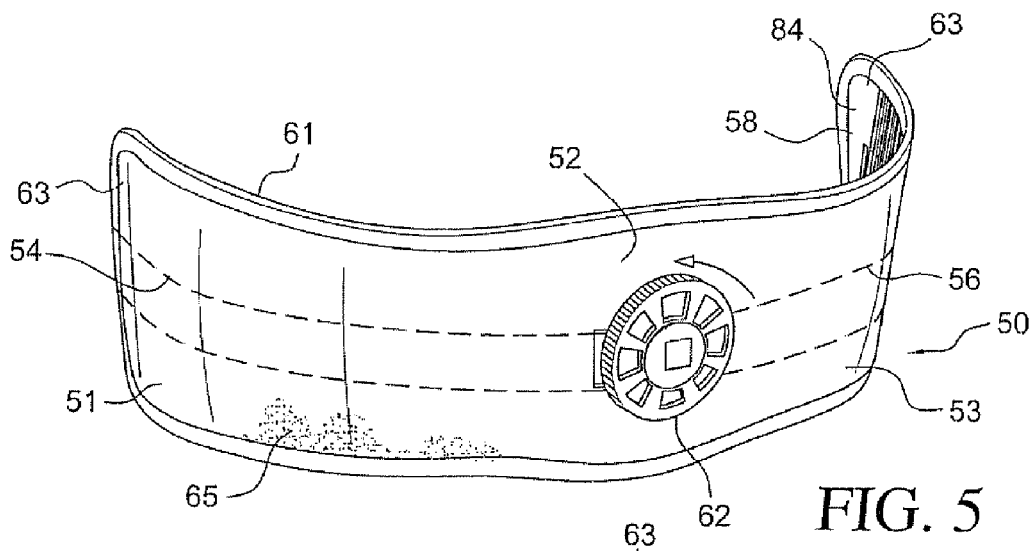
FIG. 5 is a perspective view of another embodiment of an orthopedic device in an "open" configuration.
Figure 6:
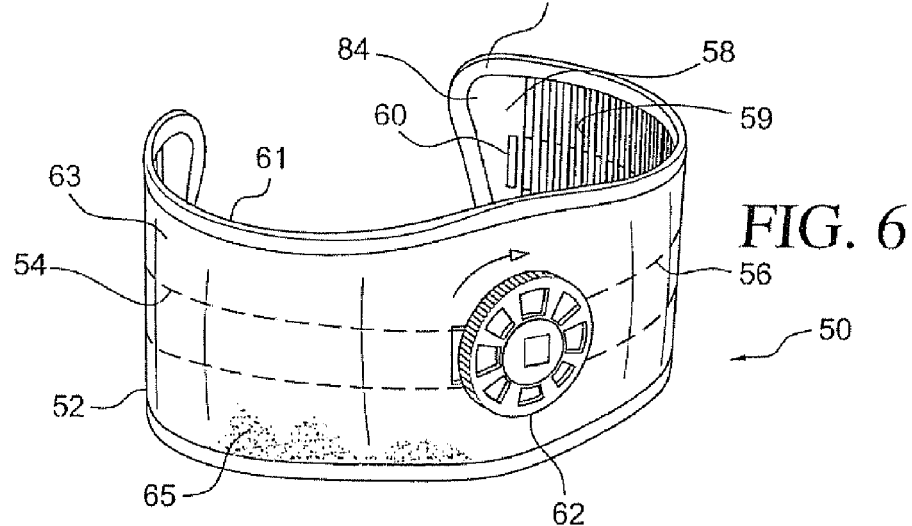
FIG. 6 is a perspective view of the orthopedic device according to FIG. 5 in a "closed" configuration.
Figure 7:
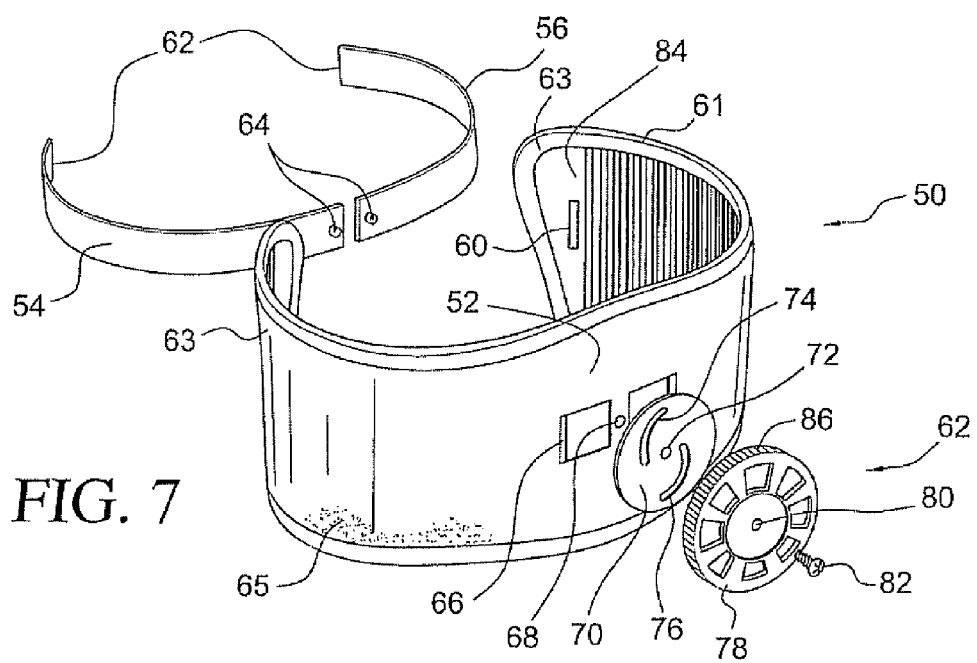
FIG. 7 is an exploded view of the orthopedic device according to FIG. 6.

In observing the embodiment of FIGS. 5-7, an embodiment of a support device 50 is shown having an adjustment system 62. This support device may be used in orthopedic or prosthetic systems. The support device 50 includes first and second segments 51, 53 depending from a central portion 52. The first and second segments 51, 53 are configured to extend away from any frame member. While the adjustment system 62 is depicted herein as being secured to the support device 50, it may be secured to the support member via a frame member, as depicted in the embodiment of FIGS. 1-4.

As exemplified in FIGS. 5 and 6, the adjustment system 62 is adapted to increase or reduce the curvature of the support device 50. For example FIG. 5 shows the support device 50 as having an open configuration which may be set prior to the support member being secured onto a leg. This may be accomplished by rotating the adjustment system 62 in a counter-clockwise direction. On the other hand, FIG. 6 shows the support device 50 in a closed configuration which is of a sufficient curvature to secure onto a leg, and in which the adjustment system 62 has been rotated in a clockwise direction.

The support device 50 of this embodiment may be constructed so as to have a resilient frame 58 including a perimeter edge 61 and end portions 63 which bound a plurality of slots 59 formed along the posterior side of the support member. An anterior covering 65 formed from a breathable textile or polymeric material covers the slots 59, and is secured to the perimeter edge 61 and the end portions 63. A clearance is generally defined between the resilient frame 58 and the anterior covering 65 at regions outside of the end portions 63 and the perimeter edge 61.

In observing FIG. 7, resilient first and second bands 54, 56 having a preformed shape are provided for being adapted to change the shape of the support device 50. The bands 54, 56 have first ends 62 which are anchored to mounts 60 located at end portions of the first and second segments 51, 53. The bands 54, 56 also define pins 64 which are defined at the second ends thereof. The bands 54, 56 are generally retained within the clearance defined between the resilient frame 58 and the anterior covering 65. The second ends 64 are generally movable relative to the support device 50.

The central portion 52 of the support device 50 defines a couple of openings 66 that are each arranged to receive the pins 64. The central portion 52 also defines an aperture 68 through which an axle 82 (such as a fastener) passes through and secures to the support device 50. The cam wheel 70 is mounted on the axle 82 via a central aperture 72, and has cam surfaces 74, 76 which engage the pins 64. Also, a dial wheel 78 is mounted onto the axle 82 via a central aperture 80 such that the cam wheel 70 is located between the support device 50 and the dial wheel 78. The dial wheel 78 has a gripping feature 86 located about the periphery thereof, and is preferably lockable in a rotational position (such as a ratchet).

The adjustment system 62 is defined by the pins 64 which engage the cam surfaces 74, 76 of the cam wheel 72, and the dial wheel 78 which locks with the cam wheel 72. It follows that rotation of the dial wheel 78 in a clock-wise direction draws the pins 64 nearer to one another and hence toward the aperture 68. This in turn causes the first and second segments 51, 53 to be drawn toward one another, thereby varying the dimension of the support device 50 to accommodate a particular anatomy.

The dial wheel 78 may be rotated in a counter-clockwise direction so as to release the support device 50 from a constricted configuration. The cam surfaces 74, 76 have limiting surfaces which represent maximum and minimum size settings of the support device 50. Therefore, a wearer is limited as to how tightly the support device 50 is applied to the anatomy so as to prevent any injury or discomfort to the wearer.

The band segments 54, 56 are preferably constructed from a resilient material, such as from plastics and metals. The band segments 54, 56 are preformed with a first curvature and may be urged into a plurality of curvatures so as to allow for a plurality of different size settings to the support member.

When urged into a tighter curvature that generally has a radius that is less than the first curvature, the band segments are intended to revert back to the first curvature once released from the tighter curvature.

As with prior embodiments, a frictional feature 84 is provided on the posterior side of the support device 50. As shown in FIGS. 6 and 7, the frictional feature 84 is preferably provided, at least in part, on the material portions of the resilient frame 58 so as to work in combination with the adjustment system 62 to maintain the support device 50 on the anatomy of the wearer.

In accordance with another embodiment, FIGS. 8 and 9 exemplify a support device 100 having a main body 102 and an adjustment system 106 which varies the curvature of a resilient band element 104 associated with the main body 102. The main body 102 is preferably formed from a resilient material and defines a main thickness with regions of reduced thickness 126. The support device 100 may be configured to accommodate a variety of anatomy sizes, as evidenced by the size A1-A2 in FIG. 8, and the size B1-B2 in FIG. 9.

The adjustment system 106 is preferably a ratchet having a handle 110 arranged to incrementally adjust a gear wheel 108 mounted on a ratchet 112 and arranged to engage the band element 104. The ratchet may comprise a variety of ratchets known to one of ordinary skill in the art including ratchet buckles, and ladder ratchets.

As shown in FIGS. 10-12, the band element 104 is retained within a channel 116 formed within the main body 102. The band element 104 has a first end 117 which is anchored to a first end 115 of the main body 102. The band element 104 has a second end portion 119 which is movable relative within the channel 116. The channel 116 has a length greater than the band element 104 in order to permit adjustment of the band element 104 therewithin.

An opening 122 is defined by the main body 102 whereat the gear wheel 108 meshes with teeth 128 formed along a surface of the band element 104. The ratchet 112 permits incremental adjustment, and pulling of the second end 119 of the band element 104 toward the second end 121 of the body member 102.

As exemplified in FIGS. 10 and 11, the radius R1 of the support device 100 in FIG. 10 is greater than the R2 of the support device 100 in FIG. 11. In the configuration of FIG. 10, the support device 100 is considered to be in an open configuration for placement of the support member on a limb. The second end 119 of the band element 104 is a distance d1 from the second end 121 of the body member 102. FIG. 11, on the other hand, shows the support device 100 in a tightened configuration in which the second end 119 of the band element 104 has been drawn a distance d2 closer to the second end 121 of the body member 102.

As with other embodiments described herein, the support member may be provided with ventilation in the form of slots 114 formed along the body member 102. Also, padding and a frictional feature may be provided by way of the padding 113 having a frictional layer 118. The padding 113 and frictional layer may of any of the types described herein.

It will be understood that according to any of the embodiments described herein, a corresponding brace having the support member may be provided without any straps which extend fully around a leg. Indeed, the support members described herein are intended to obviate the need for straps, and instead it is the support member itself which serves the dual purpose of supporting anatomy and securing a brace or corresponding structure onto the anatomy. This, of course, does not limit the embodiments described herein so that they cannot be used with straps. To the contrary, the embodiments are intended to embrace orthopedic and prosthetic devices that employ and do not employ straps such as those that circumferentially or partially circumferentially extend about anatomy.

While the foregoing embodiments have been described and shown, it is understood that alternatives and modifications of these embodiments, such as those suggested by others, may be made to fall within the scope of the invention.

The invention claimed is:

1. An orthopedic or prosthetic support device, comprising: a resilient support member adapted to extend about a limb; a tensioning element associated with the support member, and having first and second ends, the first end being fixedly secured to the support member; wherein tensioning element is anchored to the resilient support at an extreme end portion of an elongate width of the resilient support;
an adjustment system mounted on the support member and engaging the tensioning element second end, the adjustment system arranged to incrementally adjust and retain the tensioning element relative to the support member while mounted on the support member;
wherein the support member is adapted to generally conform to a limb via adjustment of the tensioning element by the adjustment system.

2. The device according to claim 1, wherein the tensioning element is adjustably retained by the support member such that the tensioning element moves within the support member upon adjustment by the adjustment system.

3. The device according to claim 1, wherein the tensioning element is elongate and extends within a channel defined by the support member.

4. The device according to claim 1, wherein the tensioning element defines an anchor located at the first end which is fixedly secured to the support member.

5. The device according to claim 1, wherein the support member defines a plurality of openings and material portions surrounding the openings, the tensioning element extending through only the material portions of the support member in a channel defined therein.

6. The device according to claim 1, wherein the support member defines a main body having a main thickness, the main body having a plurality of localized reduced thickness sections defined by a reduced thickness relative to the main thickness, the reduced thickness sections oriented generally perpendicular to a direction of the tensioning element.

7. The device according to claim 1, wherein the support member defines a first surface having a frictional feature defined by a perforated silicone coating located directly thereon.

8. The device according to claim 1, further comprising a padding element having a first side secured to a first surface of the support member, the padding element including a coating of frictional material located on a second side opposite to the first side.

9. The device according to claim 1, wherein a length of the tensioning element between the first end and the adjustment system is located within the support member.

10. The device according to claim 1, wherein the adjustment system moves the position of the second end of the tensioning element relative to the support member.

11. The device according to claim 1, wherein the adjustment system is mounted at a central portion along the elongate width of the resilient support.

* * * * *